United States Patent [19]

Economy et al.

[11] Patent Number: 5,034,190
[45] Date of Patent: Jul. 23, 1991

[54] APPARATUS FOR CONDUCTING ACCELERATED CORROSION TESTING OF NICKEL ALLOYS

[75] Inventors: George Economy, Murrysville; Richard J. Jacko, Forest Hills; Fredric W. Pement; Alfred W. Klein, both of Pittsburgh, all of Pa.

[73] Assignee: Westinghouse Electric Corp., Pittsburgh, Pa.

[21] Appl. No.: 183,260

[22] Filed: Apr. 8, 1988

Related U.S. Application Data

[63] Continuation of Ser. No. 824,910, Jan. 31, 1986, abandoned.

[51] Int. Cl.⁵ .......................................... G01N 17/00
[52] U.S. Cl. ................................. 422/53; 422/111; 422/112; 422/240; 436/6
[58] Field of Search ............... 422/53, 111, 112, 227, 422/240; 436/6; 423/657; 55/16, 492

[56] References Cited

U.S. PATENT DOCUMENTS

| | | | |
|---|---|---|---|
| 819,383 | 5/1906 | Sprague | 422/33 |
| 2,824,620 | 2/1958 | Rosset | 55/16 |
| 2,958,391 | 11/1960 | Rosset | 55/16 |
| 3,428,476 | 2/1969 | Langley et al. | 55/16 |
| 3,975,170 | 8/1976 | Keating, Jr. | 55/16 |
| 4,290,872 | 9/1981 | Monter | 204/195 F |
| 4,361,536 | 11/1982 | Leopardi | 422/33 |
| 4,416,740 | 11/1983 | Schulze-Berge | 204/44.6 |
| 4,440,862 | 4/1984 | Cheng et al. | 436/6 |

FOREIGN PATENT DOCUMENTS 966122 8/1964 United Kingdom ..................... 55/16

OTHER PUBLICATIONS

G. P. Airey, "The Stress Corrosion Cracking Performance of Inconel Alloy 600 in Pure and Primary Water Environments", a paper circulated within the Westinghouse Research Development Center.
G. P. Airey, "Optimization of Metallurgical Variables to Improve Corrosion Resistance on Inconel Alloy 600", EPRI NP-3051, 7/83.
R. Bandy et al., "Stress Corrosion Cracking of Inconel Alloy 600 in High Temperature Water-an Update", Corrosion, vol. 40, pp. 425-430, 1984.
D. Van Rooyen, "Review of the Stress Corrosion Cracking of Inconel 600", Corrosion, vol. 31, pp. 327-337 (1975).
Eduardo Serra, "Stress Corrosion Cracking of Alloy 600", Electric Power Research Institute Document NP-2114-SR, dated Nov. 1981.

(List continued on next page.)

Primary Examiner—Robert J. Hill, Jr.

[57] ABSTRACT

Both an improved method and apparatus for determining, on an accelerated basis, the susceptibility of a nickel-based alloy to suffer stress corrosion cracking within a steam generator environment is disclosed herein. The method generally comprises the steps of subjecting a mechanically stressed specimen of the alloy to a mixture of steam and hydrogen at a temperature of between about 365° C. to 435° C., wherein the partial steam pressure is between about 10.4 MPa to 30.4 MPa, and the partial hydrogen pressure is between about 32 kPa to 500 kPa. The improved testing apparatus of the invention generally comprises a vessel for containing a stressed specimen and a pressurized atmosphere formed of steam and hydrogen, and an inlet cell for injecting a selected amount of hydrogen into the pressurized atmosphere of the vessel which includes a diffusion membrane which is permeable to hydrogen but impermeable to the remainder of the pressurized atmosphere. The inlet cell has a tubular housing having a wall formed from a thin layer of hydrogen permeable palladium-silver alloy. The tubular housing contains a gas permeable sponge formed by sintered particles of stainless steel to prevent the thin layer of palladium-silver alloy used in the hydrogen diffusion membrane from imploding in response to the pressure within the vessel.

8 Claims, 2 Drawing Sheets

OTHER PUBLICATIONS

T. S. Bulischeck and D. Van Rooyen, "Stress Corrosion Cracking of Alloy 600 Using the Constant Strain Rate Test", *Corrosion*, vol. 37, pp. 597–607 (1981).

D. M. Himmelblau, "Solubilities of Inert Gases in Water", *Journal of Chemical and Engineering Data*, vol. 5, pp. 10–15 (1960).

"Standard Practice for Aqueous Corrosion Testing of Samples of Zirconium and Zirconium Alloys", American Society for Testing and Materials Document Number G2-81, dated 1981.

H. Coriou et al., "Corrosion Fissurante sous Contrainte de l'Inconel dans l'Eau a Haute Temperature", presented at the 3rd Colloquium of Metallurgy–Corrosion, of Commissariat a l'Energie Atomique, France.

APPARATUS FOR CONDUCTING ACCELERATED CORROSION TESTING OF NICKEL ALLOYS

This application is a continuation of application Ser. No. 06/824,910, filed Jan. 31, 1986, now abandoned.

BACKGROUND OF THE INVENTION

1. Field of the Invention

This invention generally relates to a method and apparatus for testing the susceptibility of a nickel-based alloy to undergo stress corrosion cracking within a high temperature water environment. It is particularly useful in predicting, on a substantially accelerated basis, when the Inconel ® heat exchanger tubes of a nuclear steam generator will crack as a result of intergranular stress corrosion.

2. Description of the Prior Art

Methods and devices for determining the susceptibility of a nickel-based alloy to stress corrosion cracking within a steam generator environment are known in the prior art. Such tests are very useful in nuclear steam generator maintenance, because they provide an indication as to when certain preventative maintenance procedures, such as sleeving, should be initiated within the heat exchanger tubes of such generators. Such maintenance procedures prevent radioactive water from the primary side of the generator from leaking out of cracked heat exchanger tubes and contaminating the non-radioactive water used in the secondary side of the generator which forms the steam which ultimately drives the electric turbines in the plant. However, before the utility of such test methods can be fully appreciated, a more complete understanding of the structure and maintenance of nuclear steam generators is necessary.

Nuclear steam generators are comprised of three principal parts, including a secondary side, a tubesheet in which a plurality of U-shaped tubes are mounted, and a primary side. The tubesheet and U-shaped tubes hydraulically isolate the primary from the secondary sides of the steam generator while thermally connecting them together, so that heat from the radioactive water in the primary side is transferred to the non-radioactive water in the secondary side. This heat transfer is accomplished by the U-shaped tubes mounted in the tubesheet which extend throughout the secondary side of the steam generator. The inlet and outlet ends of these U-shaped tubes are mounted in the side of the tubesheet that faces the primary side of the generator. The primary side in turn includes a divider plate that hydraulically isolates the inlet ends of the U-shaped tubes from the outlet ends. Hot, radioactive water heated by the nuclear reactor is admitted into the section of the primary side containing all the inlet ends of the U-shaped tubes. This hot water flows through these inlets, up through the tubesheet, and circulates within and around the U-shaped tubes that extend within the secondary side of the steam generator. This hot, radioactive water transfers its heat through the walls of the U-shaped tubes to non-radioactive feed water present in the secondary side of the generator, thereby converting this feed water into non-radioactive steam. After the nuclear-heated water circulates through the U-shaped tubes, it flows back through the tubesheet, through the outlets of the U-shaped tubes, and into the outlet section of the primary side, where it is circulated back to the nuclear reactor.

The heat exchanger tubes of such nuclear steam generators can suffer a number of different types of corrosion degradation, including intergranular stress corrosion cracking. In situ examination of the tubes within these generators has revealed that most of this intergranular stress corrosion cracking occurs around the tubesheet region of the generator, where the inlet and outlet ends of the U-shaped tubes extend through bores in the tubesheet. Often there is some amount of annular space between the walls of the tube-receiving bores in the tubesheet and the outer walls of the tubes themselves. Experience has shown that potentially corrosive sludges can accumulate on the upper surface of the tubesheet and collect in these annular spaces over long periods of time. To prevent these potentially corrosive sludges from collecting within these annular spaces from the effect of gravity, the heat exchanger tubes are often radially expanded by means of a mechanical or a hydraulic mandrel in order to minimize the clearance between the outer walls of the tubes and the inner walls of the bores in the tubesheet through which they extend. However, some of these potentially corrosive sludges may still collect in these very small spaces between the tubes and the bores of the tubesheets. Moreover, the relatively poor hydraulic circulation of the water in these regions tends to maintain the sludge in these crevices and to create localized "hot spots" in the tubes adjacent the sludge. The heat radiating from these "hot spots" may assist in the corrosion processes that operate on the exterior surfaces of the heat exchanger tubes in chemical combination with corrosive species in the sludge. While most nuclear steam generators include blow-down systems for periodically sweeping the sludge out of the generator vessel, the sludges in the annular crevice regions are not easily swept away the hydraulic currents produced by such systems. Despite the fact that the heat exchanger tubes of such nuclear steam generators are typically formed from corrosion-resistant Inconel ®, the constant exposure to corrosive sludges and heat, in combination with the mechanical stresses induced in these walls as a result of the mechanical or hydraulic expansion, can ultimately cause the heat exchange tubes to corrode and crack due to intergranular stress corrosion cracking. This, in turn, can allow radioactive water from the primary side of the steam generator to leak into the secondary side of the generator, thereby radioactively contaminating the steam produced by the generator which turns the blades of the electric turbines of the plants.

Such radioactive contamination of the generator steam can be avoided if certain maintenance procedures, such as tube sleeving, are undertaken before the walls of the tubes crack. In such sleeving operations, a reinforcing sleeve is slid up the heat exchanger tubes in the sections of the tubes surrounded by the tubesheet, and rolled and brazed onto the inner walls of the tubes. But, while such sleeving operations are very effective in extending the useful lifetime of the nuclear steam generator, they are also quite expensive. The steam generator has to be completely shut down and taken off-line (which can cost over $500,000 per day), and very specialized tools and procedures must be utilized to install such sleeves within the radioactive environment inside the steam generator. It is therefore desirable that such sleeving operations be undertaken only when stress corrosion cracking is imminent so that the number of times that the generator must be shut-down for an a maintenance operation is kept to a minimum.

The prior art stress-corrosion tests were developed as a result of the need to predict when stress-corrosion cracking was likely to occur in the tubesheet region of a particular nuclear steam generator. Such tests generally involved subjecting a mechanically stressed sample of the particular type of Inconel ® used in the heat exchanger tubes of a particular steam generator to heated water having hydrogen gas dissolved within it. Typically, the water used in the test was heated to a temperature of between 300° C. and 365° C. (or 572° F. to 689° F.). At all times, the water was maintained in a liquid phase by maintaining the atmosphere within the test vessel at a pressure of approximately 15.8 MPa (or 2,200 psi). To simulate the water chemistry inside a nuclear steam generator, substantially pure water with a small amount of hydrogen dissolved therein was used. The radioactive environment of the primary side of such nuclear generators radiolytically creates small amounts of free hydrogen and oxygen gas in this water. To minimize the amount of radiolytically produced oxygen in the generator water, a measured amount of hydrogen gas is deliberately dissolved into it. Such hydrogen curbs the radiolytic production of free oxygen in accordance with Le Chatelier's principle. In steam generators, approximately 25 to 50 cc of hydrogen (as measured at 0° C. and 1 atmosphere absolute pressure) is dissolved into every kilogram of water used in the primary coolant within the steam generator. To simulate this hydrogen component, the partial hydrogen gas pressure in the mixture of pressurized water and hydrogen in the test vessel was initially adjusted to between 250 and 1300 kPa at room temperature.

The foregoing test conditions have been found to produce corrosion cracking in stressed samples of Inconel ® approximately ten times faster than it would take for these samples to exhibit cracking in a real-time mode.

Unfortunately, such prior art testing methods are not without significant shortcomings. Even though such test methods corrode the test samples in an accelerated mode, the exposure times can still be quite long for certain types of heat-treated Inconel ®. For example, for certain types of heat-treated Inconel ® heat exchanger tubes, the exposure time required to produce cracking in even a very highly stressed sample may be as long as 40,000 hours. Secondly, because of its small molecular size, the free hydrogen within the test vessel will tend to slowly diffuse through the seals and walls of the vessel, a phenomenon which necessitates the use of refreshed autoclave systems. Such systems are complex and expensive, and require such components as continuously overpressured make-up tanks, high-pressure pumps, and effluent coolers.

Clearly, there is a need for a testing method and apparatus which is capable of determining, in a greatly accelerated mode, the susceptibility of nickel-based alloys to stress corrosion cracking in simulated steam generator environments. Ideally, such a test method should be able to operate in a predictive mode that is an order of magnitude faster than known stress corrosion cracking tests, while accurately maintaining a calibrated amount of free hydrogen within its test vessel throughout the duration of the test. Finally, it would be desirable if such a vastly accelerated test method could be conducted with a simple and relatively inexpensive test apparatus.

SUMMARY OF THE INVENTION

The invention is both a method and an apparatus for conducting an accelerated test of the susceptibility of a metal to stress corrosion cracking within a steam generator environment. The method of the invention generally comprises subjecting a mechanically stressed specimen of the metal to a mixture of steam and hydrogen at a temperature of between about 365° C. to 435° C., wherein the typical partial steam pressure is between about 10.4 MPa to 30.4 MPa, and the typical partial hydrogen pressure is between about 32 kPa to 500 kPa.

In a more preferred embodiment of the method, the stressed specimen is subjected to a mixture of steam and hydrogen at a temperature that is typically between about 375° C. to 425° C., and a partial steam pressure of between 15.7 MPa to 25.7 MPa, and a partial hydrogen pressure typically between about 50 kPa to 100 kPa. Finally, in the most preferred embodiment of the method, the metal is subjected to a mixture of steam and hydrogen at a temperature of about 400° C., wherein the partial pressure of the steam is about 20.4 MPa, and the partial pressure of the hydrogen is about 76 kPa. This method is particularly useful for testing the susceptibility of Inconel ® heat exchanger tubes to crack as a result of intergranular stress corrosion cracking on an accelerated basis. Specifically, it has been discovered that stressed specimens of Inconel ® subjected to the foregoing pressurized steam and hydrogen conditions will exhibit stress corrosion cracking approximately 100 times faster than on a real-time basis.

The improved testing apparatus of the invention generally comprises a vessel for containing a stressed specimen of the metal to be tested along with a pressurized atmosphere formed in part by hydrogen, and a means for injecting a selected amount of hydrogen into the pressurized atmosphere of the vessel, including a diffusion membrane that is permeable to hydrogen but impermeable to the remainder of the components of the pressurized atmosphere. The membrane is preferably formed from an alloy containing palladium and silver, and may be between 0.1 and 0.15 mm thick. This membrane may be mounted on the wall of an inlet cell whose outer walls communicate with the pressurized atmosphere inside the vessel, but whose inner walls communicate with a source of hydrogen gas. Additionally, the housing may include a gas-permeable solid for supporting the diffusion membrane against the pressure exerted on it by the pressurized atmosphere of the vessel. In the preferred embodiment, this gas permeable solid is an open-celled metal sponge having a smooth surface which is formed by sintering a powder of number 316 stainless steel.

The improved testing apparatus may further include a means for monitoring the partial pressure of the hydrogen within the vessel that includes a housing whose outer surface communicates with the atmosphere within the vessel, and whose inner surface communicates with a pressure sensor means. At least a portion of the wall of the housing may be formed from a hydrogen diffusion membrane of the same composition and thickness as the diffusion membrane used to inject hydrogen within the vessel. Finally, the same type of open-celled metallic sponge used in the inlet cell may be placed within the housing to support the hydrogen diffusion membrane from the pressure exerted upon it by the pressurized atmosphere within the vessel.

The use of a metallic sponge having a smooth outer surface to support the relatively thin and fragile membrane, as opposed to a rigid mechanical cage-like structure, helps prevent the membrane from being damaged by eliminating local points of stress between the surface of the membrane and the support structure within the walls.

DETAILED DESCRIPTION OF THE PREFERRED EMBODIMENT

Figure 1:
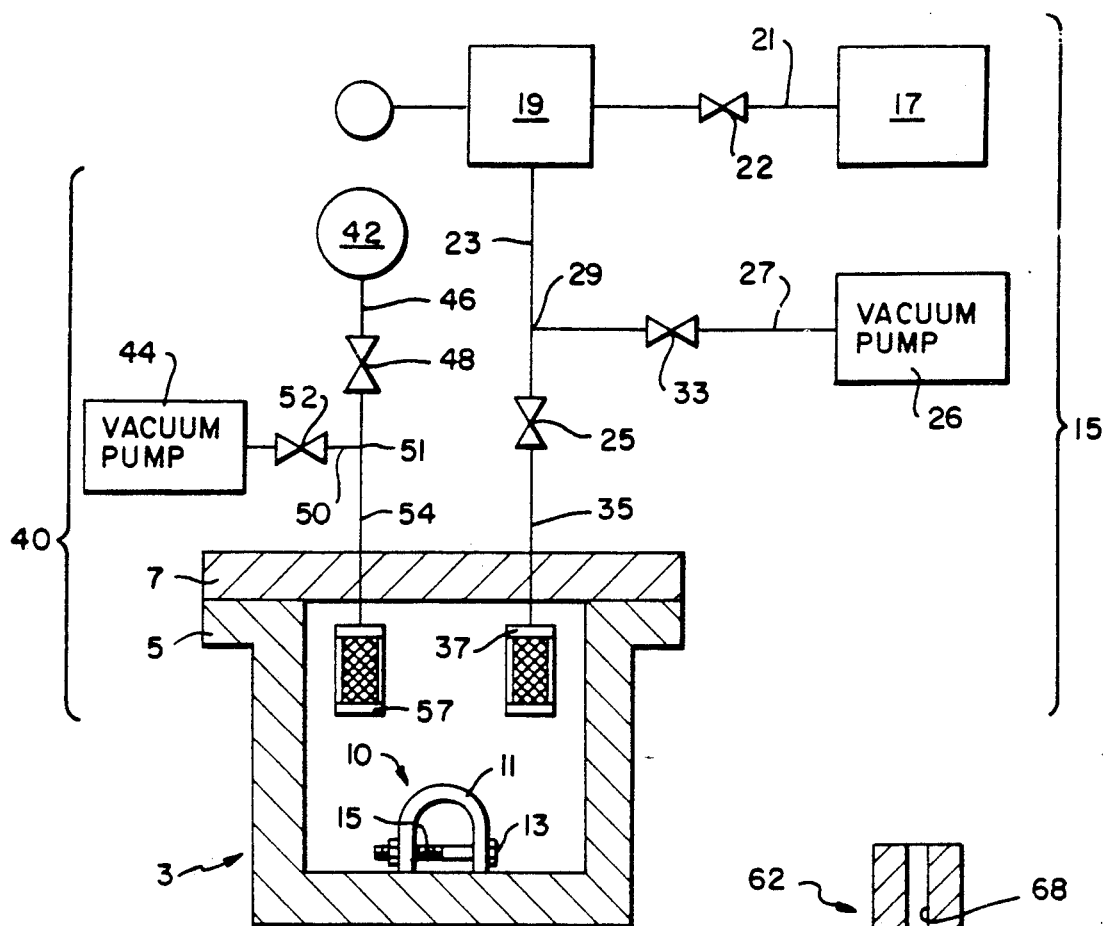
FIG. 1 is a schematic diagram of the apparatus used to conduct the tests of the invention.
Figure 2:
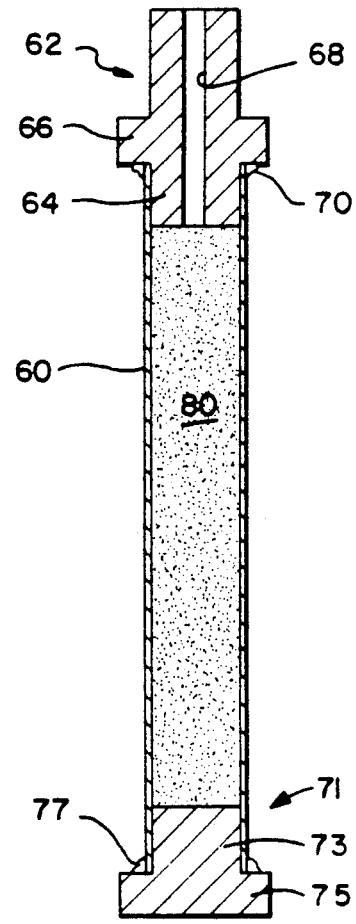
FIG. 2 is a cross-sectional side view of the structure of the hydrogen inlet and outlet cells used in the testing apparatus illustrated in FIG. 1.

FIGS. 1 and 2, wherein like numbers illustrate like components throughout all the several figures, illustrate the improved testing apparatus of the invention.

The testing apparatus 1 includes a vessel 3, which may be any one of a number of commercially available autoclaves, having a container 5 and a lid 7 that may be bolted thereover in sealing engagement. In the preferred embodiment, the vessel or autoclave 3 used has a tolerance of 5,225 psi at 427° C., and is manufactured by Autoclave Engineers, Inc., located in Erie, Pa. The specimen or specimens 10 to be tested are placed at the bottom of the container 5 in the position shown. Preferably, the specimens are in the form of a short section of tubing which has been cut lengthwise so that its cross-section is in the form of a semicircle. To induce stresses into the specimen, the convex side of the split tube is bent around a 2.5 cm diameter mandrel in a "U" shape in order to strain the inner diameter of the split tube. To maintain the stress pattern generated by the U bend 11, a nut and bolt combination 13 is affixed between the legs of the U, and the bolt is tightened until the distance between the two legs is 2.5 cm.

In order to maintain a constant, selected partial pressure of hydrogen within the container 5 during the testing procedure, the apparatus 1 is provided with a hydrogen inlet control 15. This hydrogen inlet control 15 includes a source of pressurized hydrogen 17 which is connected to a vacuum regulator 19 by way of a conduit 21. Conduit 21 includes a ball-type valve 22 for disconnecting the inlet of the regulator 19 from the pressurized hydrogen source 17 when desired. In the preferred embodiment, a Model 3491 vacuum regulator manufactured by the Matheson Company located in East Rutherford, N.J. can be used. The outlet of the regulator 19 is connected to a conduit 23 which in turn is connected to the inlet of another ball-type valve 25. A vacuum pump 26 is pneumatically connected to the regulator outlet conduit 23 by a further conduit 27 which forms a T joint at point 29. Vacuum pump 26 serves two purposes. First, during the start-up phase of the operation of the apparatus, 1, pump 26 is used to draw off all non-hydrogen gases in the system through line 27' having a valve 27. Second, during the operation of the apparatus 1, pump 26 bleeds off small amounts of hydrogen (which backs up against the inlet cell 37) to assist the vacuum regulator 19 in maintaining a hydrogen pressure at the inlet side of the valve 25 which is less than atmospheric pressure. In the preferred embodiment, vacuum pump 26 may be any one of a number of pumps capable of generating vacuums of 10 mm Hg or less. A metering valve 33 is provided between the vacuum pump 26 and the conduit 23 to control the amount of vacuum pressure that the pump 26 exerts on the rest of the hydrogen inlet control 15.

The outlet side of the valve 25 is connected to an inlet cell 37 by way of a further conduit 35. As will be described in more detail hereinafter, the inlet cell 37 includes a diffusion membrane that is permeable to gaseous hydrogen, but impermeable to steam. Accordingly, the inlet cell 37 will diffuse gaseous hydrogen into the interior of container 5 to whatever pressure the vacuum regulator 19 is set. Because of the provision of a pressure regulator 19 and vacuum pump 26 in the hydrogen inlet control 15, the pressure of the hydrogen injected into the container 5 may be accurately adjusted to inject hydrogen at less than atmospheric pressure.

The testing apparatus 1 further includes a hydrogen pressure monitor 40 for providing a continuous visual display of the partial pressure of the hydrogen within the container 5. Generally, the hydrogen pressure monitor includes a pressure gauge 42 that is connected to both a vacuum pump 44, and a detector or outlet cell 57 which is virtually identical in structure to the inlet cell 37. The outlet of the pressure gauge 42 is connected to the inlet of a ball-type valve 48 by means of a conduit 46. The vacuum pump 44 is connected to the outlet of the valve 48 through another conduit 50 at T-joint 51. Another ball-type valve 52 is provided in the conduit 50 for selectively isolating the vacuum pump 44 from the gauge 42 and detector cell 57. Finally, a conduit 54 connects the T-joint 51 to the outlet or detector cell 57, as indicated. In the preferred embodiment, the pressure gauge 42 is a Model 63-5601 pressure indicator, manufactured by the Matheson Company located in East Rutherford, N.J. All of the conduits used in both the hydrogen inlet control 15 and the hydrogen pressure control 40 are formed from stainless steel tubing having an inner diameter of about 3 mm. In order to minimize the time it takes to evaluate the hydrogen inlet control 15 and the pressure monitor 40, the parts which form them should be sized so that their total internal volumes are as small as practical. FIG. 2 is a cross-sectional view of the structure of both the inlet cell 37 and the outlet or detector cell 57. Generally, each of these cells includes a tubular housing 60 which is preferably 0.127 mm (or 5 mils) thick and formed from an alloy consisting of 75% palladium and 25% silver. A thickness of 0.127 mm is thin enough to pass hydrogen at the rates required by the test, yet thick enough to have adequate structural strength. Additionally, an alloy formed from 75% palladium and 25% silver is not only substantially permeable to hydrogen, but is also highly resistant to corrosion. Each of these cells includes a gas-conducting upper cap 62 having a cylindrical insert 64 whose outer diameter is very nearly the inner diameter of the housing 60. This insert 64 is preferably inserted down into the upper end of the tubular housing 60 until the annular shoulder 66 of the cap 62 engages the upper edge of the housing 60 in the position shown. To conduct hydrogen gas into or out of the interior of the housing 60, the upper cap 62 includes a centrally disposed bore 68. A nickel-gold weldment 70 circumscribes the juncture between the underside of the annular shoulder 66 and the top outer edge of the housing 60 in order to provide a gas-tight seal between the upper cap 62 and the housing 60 in this region. In the preferred embodiment, the welding material used is 88% gold and 12% nickel to prevent the introduction of impurities into the cells 37 and 57.

Each of the cells further includes a lower cap 71. This lower cap 71 includes a cylindrical plug 73 whose outer diameter is very close in size to the inner diameter of the housing 60. This cylindrical plug 73 is inserted up into the bottom portion of the housing 60 until the bottom edge of the housing 60 engages the annular shoulder 75 of the cap 71. Again, a nickel-gold weldment 77 of the same type used in weldment 70 circumscribes the junction between the lower edge of the housing 60 and the annular shoulder 75 of the lower cap 71 to provide a gas-tight seal between the cap 71 and the housing 60 in this region.

To support the hydrogen-diffusion membrane formed by the thin, tubular palladium-silver housing 60, a sintered, stainless steel sponge 80 is disposed within the interior of the housing 60. The sponge 80 is formed from small particles of number 316 stainless steel that have been sintered until particles adjacent one another have become fused together. The resulting structure is an open-celled, sponge-like structure having a smooth surface that is easily permeated by hydrogen gas, but which also displays a considerable amount of compressive strength. In the preferred embodiment, the stainless steel particles forming the sponge 80 are sintered in accordance with well-known powder metallurgy practices until an average pore size of 10 microns is achieved. The metallic sponge 80 not only prevents the relatively thin, tubular housing 60 from collapsing in response to the 3,000 psi steam pressure within the vessel 3, but it also offers much more uniform support along the inner surface of the tubular housing 60 than, for example, a perforated support tube or mechanical cage-like structure. Such uniform support throughout all points of the inner surface of the tubular housing 60 prevents localized compressive stresses from occurring when pressurized steam presses against the outer surface of the housing 60 which could puncture and destroy it.

The corrosion resistance of the palladium-silver housing 60 and weldments 70, 77 make the inlet and outlet cells 37, 57 suitable for the dual use as reference electrodes while injecting or withdrawing hydrogen out of the pressurized atmosphere within the vessel 3. When such dual use is desired, conduits 35 and 54 should be palladium plated, as should the stainless steel upper and lower caps 62 and 71 of each cell.

Now that the testing apparatus 1 of the invention has been described in detail, a preferred embodiment of the testing method will be set forth.

In the first step of the test method, one or more test specimens 10 are stressed in the manner hereinbefore described, and the resulting U-bends 11 are placed into the bottom of a container 5 of the vessel or autoclave 3. Next, high-purity, demineralized water having a conductivity of less than 1 microS/cm is added to the container 5, and the lid 7 is securely bolted thereon. The vessel or autoclave 3 is then heated and steamed in order to de-gas the environment within the container 5. The temperature of the steam within the vessel or autoclave 3 is raised until it is approximately 400° C. Once this has been achieved, the pressure within the autoclave is adjusted until it is approximately 20.7 MPa.

After the desired steam temperature and pressure has been achieved, the hydrogen inlet control 15 is actuated by opening the valves 22 and 35, and by adjusting the pressure regulator 19, the vacuum pump 26 and the metering valve 29 until the pressure of the hydrogen within the inlet cell 37 is 76 kPa. In British units, this amounts to 11 pounds per square inch. After a time period of about an hour or so, the hydrogen pressure monitor 40 is actuated to determine whether or not the hydrogen inlet control 15 has achieved the desired partial pressure of hydrogen within the container 5. This is accomplished simply by opening the valves 48 and 52, and by actuating the vacuum pump 44. After the vacuum pump 44 draws substantially all of the air out of the conduits and valves 46, 48, 50, 52, and 54, as well as the air out of the detector cell 57, it is deactuated. The pressure gauge 42 is then observed. If the hydrogen inlet control 15 is operating properly, the gauge 42 should indicate a partial hydrogen pressure of 76 kPa within a short period of time. The visual gauge 42 is then periodically monitored to ensure that the hydrogen inlet control 15 continues to accurately maintain a partial hydrogen pressure of 76 kPa within the vessel 5 throughout the duration of the test.

The balance of the test method consists of periodically shutting down the vessel or autoclave 3, evacuating the pressurized steam therefrom, and extracting and examining the specimens contained therein at regular time intervals. In the preferred embodiment of the testing method, the samples are examined not at uniform time periods, but at irregular periods which become shorter when a group of specimens begins to exhibit cracking. The inspections are performed by means of a microscope at magnifications from 10 to 100 x as needed. Specimens that have initiated intergranular stress corrosion cracking are removed from the test, and the balance of the specimens are returned to test.

Figure 3:
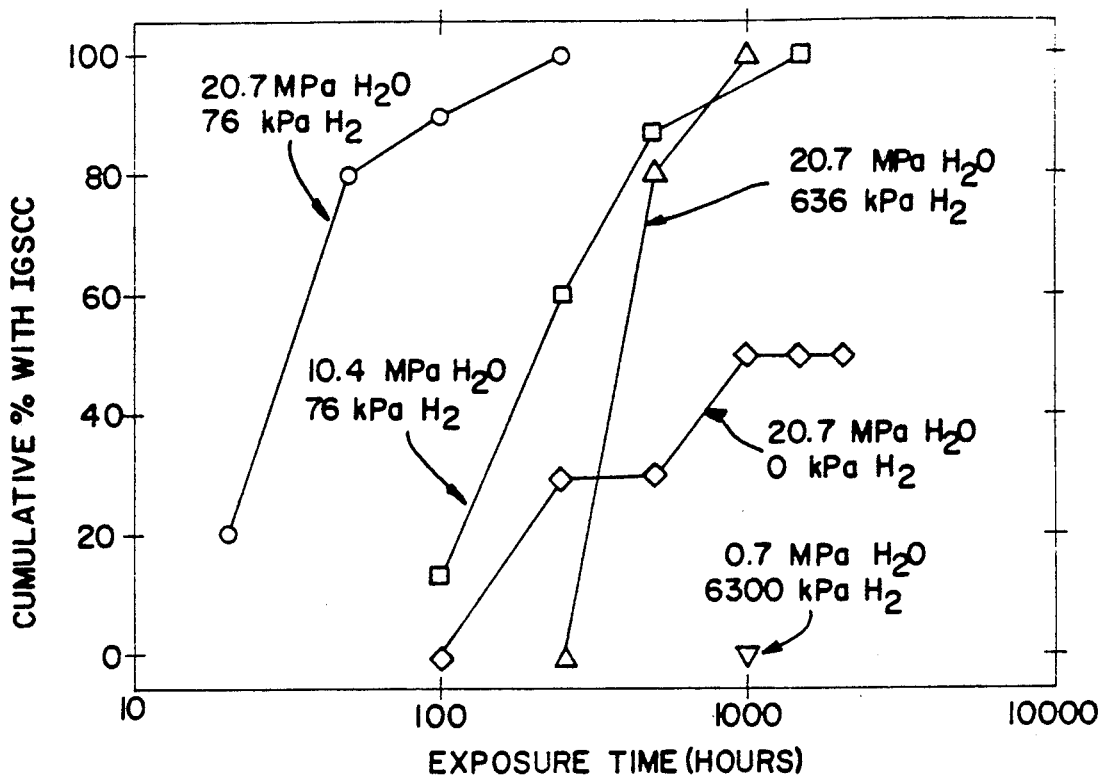
FIG. 3 is a graph illustrating the relative times at which various specimens of stressed Inconel ® exhibited stress corrosion cracking (abbreviated as "IGSCC" along the ordinate of this graph) at different combinations of steam and hydrogen pressure.
Figure 4:
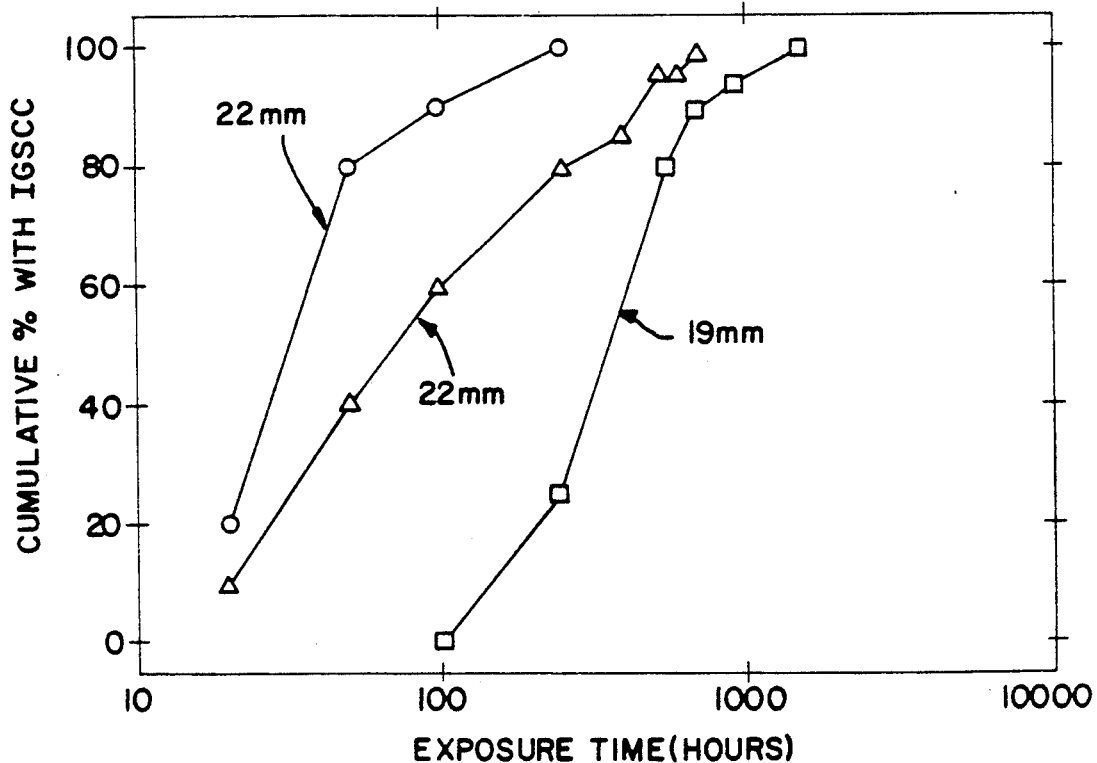
FIG. 4 is a graph comparing the speed with which three different types of heat exchanger tubing exhibited stress corrosion cracking under the steam and hydrogen conditions of the invention.

FIGS. 3 and 4 summarize the data that led to the discovery of the improved testing method of the invention. Specifically, FIG. 3 compares the rate at which a group of U-bent specimens of Inconel ® alloy 600 tubing exhibits stress corrosion cracking at various combinations of steam and hydrogen pressure. In all cases, the temperature of the steam and hydrogen mixture was maintained at 400° C. throughout the duration of the test.

While these test results indicate a roughly linear relationship between the pressure of the steam used in the tests and the rate at which the test specimens exhibit stress corrosion cracking, they also indicate a non-linear relationship between the amount of admixed hydrogen in the steam atmosphere used, and the speed with which the specimens crack. Specifically, while the test conducted at 10.4 MPa steam and 76 kPa hydrogen takes more than twice as much time as the 20.7 MPa steam and 76 kPa hydrogen combination used in the invention, the addition or subtraction of the hydrogen pressure appears, in both cases, to retard the formation of stress corrosion cracking in the specimens. (Compare the results at 20.7 MPa steam and 636 kPa hydrogen and 20.7 Mpa steam and 0 kPa hydrogen with the 20.7 MPa steam and 76 kPa hydrogen combination of the invention).

The tables below and the graphs of FIG. 4 manifestly illustrate the superiority of the testing method of the invention in inducing stress corrosion cracking in different sizes and heats of Inconel ® alloy 600 over prior art testing methods.

| Results for Alloy 600 Reverse U-Bends (RUB's) Made From 22 mm Tubing in 400° C. Test With Steam at 20.7 MPa and H₂ at 76 kPa | | | | | | |
|---|---|---|---|---|---|---|
| | Number of RUB's with IGSCC/Number of RUB's Tested | | | | | |
| Heat Number Hours Exposure | 1019 Set 1 | 1019 Set 2 | 1991 | 2650 Set 1 | 2650 Set 2 | 2721 |
| 20 | — | 1/5 | — | — | 0/5 | — |
| 50 | — | 4/5 | — | — | 0/5 | — |
| 100 | 5/5 | 4/5 | 2/5 | 5/5 | 1/5 | 1/5 |
| 250 | | 5/5 | 5/5 | | 2/5 | 2/5 |
| 400 | | | | | 4/5 | — |
| 500 | | | | | — | 5/5 |
| 550 | | | | | 4/5 | |
| 650 | | | | | 5/5 | |

Note: A dash (—) indicates that no inspection was performed at the indicated hours of exposure.

| Results for Alloy 600 Reverse U-Bends (RUB's) Made From 19 mm Tubing in 400° C. Test With Steam at 20.7 MPa and H₂ at 76 kPa | | | | |
|---|---|---|---|---|
| Heat Number | Number of RUB's with IGSCC/Number of RUB's Tested | | | |
| Exposure Hours | 2616 | 7735 | 7805 | 9861 |
| 100 | 0/5 | 0/5 | 0/5 | 0/5 |
| 250 | 4/5 | 0/5 | 1/5 | 0/5 |
| 500 | 5/5 | 3/5 | 5/5 | 3/5 |
| 600 | | 3/5 | | 5/5 |
| 900 | | 4/5 | | |
| 1600 | | 5/5 | | |

Note that even the most corrosion resistant of the specimens (heat number 7735 of the 19 mm tubing) had exhibited stress corrosion cracking by 1600 hours. By contrast, when hydrogen-containing water is used at 368° C., the results are as follows:

| Results for Alloy 600 Reverse U-Bends (RUB's) in H₂-Containing* Water Tests at 368° C. | | | | | | |
|---|---|---|---|---|---|---|
| Heat No. | Number of RUB's with IGSCC/Number of RUB's Tested | | | | | |
| Hours | 22 mm (⅞ in.) OD Heats | | | | 19 mm (¾ in.) OD Heats | |
| Exposure | 1019 | 1991 | 2650 | 2721 | 7735 | 9861 |
| 250 | 0/5 | 0/5 | 0/5 | 0/5 | 0/5 | 0/5 |
| 440 | — | — | — | — | — | — |
| 500 | 5/5 | 3/5 | 3/5 | 0/5 | 0/5 | 0/5 |
| 1000 | | 4/5 | 4/5 | 0/5 | 0/5 | 0/5 |
| 1400 | | 4/5 | 4/5 | 0/5 | 0/5 | 0/5 |
| 1500 | — | — | — | — | — | — |
| 2000 | | 4/5 | 4/5 | 0/5 | 0/5 | 0/5 |
| 3000 | | 5/5 | 4/5 | 1/5 | 0/5 | 0/5 |
| 4000 | | | 4/5 | 1/5 | 0/5 | 0/5 |

Note: A dash (—) indicates that no inspection was performed at the indicated hours of exposure
*No H₂ added. Measured H₂ pressure at end of a 500 hour test exposure was about 1.0 kPa.

Even after 4,000 hours none of the 19 mm specimens of heat number 7735 (or even heat number 9861) exhibited any stress corrosion cracking.

While specific embodiments of both the method and apparatus of the invention have been set forth, it is expected that various modifications and re-arrangements of the invention will occur to those skilled in the art. For example, alterations may be made of the preferred temperature, pressure and density of the steam and hydrogen used while still achieving much of the beneficial results of the invention. Additionally, other support structures than a sponge of sintered stainless steel may be used in the inlet and outlet cells, and other corrosion-resistant palladium-base alloys (or unalloyed palladium) may be used as the hydrogen-permeable membranes in the inlet and outlet cells 37 and 57. All such modifications, changes, and their equivalents are intended to fall within the scope of the claims of this patent.

We claim:

1. An improved testing apparatus for determining, on an accelerated basis, the susceptibility of a metal to stress corrosion cracking, comprising:
    (a) vessel means for providing pressurized steam and for containing a stressed specimen of a metal and an atmosphere formed from the pressurized steam and hydrogen;
    (b) an inlet cell positioned and arranged in fluid communication with said vessel for injecting a selected amount of hydrogen into the vessel, including a diffusion membrane which is permeable to hydrogen but not to steam, wherein said inlet cell is fluidly connected to a source of pressurized hydrogen through a first conduit;
    (c) an outlet cell positioned and arranged in fluid communication with said vessel for monitoring the amount of hydrogen within the vessel, also including a diffusion membrane which is permeable to hydrogen but not to steam, and
    (d) a hydrogen inlet control for maintaining the partial pressure of the hydrogen within the vessel to a selected value that is less than atmospheric pressure, including a vacuum regulator means fluidly connected across said first conduit, and a vacuum pump means fluidly connected to said first conduit at a point between said vacuum regulator means and said inlet cell for both evacuating hydrogen from the vessel during start-up of the apparatus, and for assisting the vacuum regulator in maintaining sub-atmospheric pressures of hydrogen within the vessel when said selected partial pressure is less than atmospheric.

2. The apparatus of claim 1, wherein said membranes each include a sheet of an alloy formed from about 25% silver and 75% palladium, each of said sheets being between about 0.1 and 0.15 mm thick.

3. The apparatus of claim 2, wherein each of said cells includes a gas permeable solid having an average pore size of about 10 microns constructed and arranged for supporting its respective membrane against pressure applied thereon by steam from within the vessel, and wherein at least one of said cells includes a layer of a palladium that covers all non-membrane parts of said cell, and wherein the palladium alloy in the membrane of said cell, and the layer of palladium that covers all other parts of said cell may be used as an electrode.

4. The apparatus of claim 3, wherein said gas permeable solid is a sponge of stainless steel formed from sintered stainless steel particles.

5. An improved testing apparatus for determining, on an accelerated basis, the susceptibility of a nickel-based alloy to stress corrosion cracking when exposed to the primary water of a nuclear steam generator, comprising:
    (a) vessel means for providing pressurized steam and for containing a stressed specimen of a nickel-based alloy and an atmosphere formed from the steam having a partial pressure of between about 10.7

MPa and 30.7 Pa, and hydrogen having a partial pressure of between about 50 kP 100 kPa;

(b) means for maintaining the partial pressure of the hydrogen within the vessel to a value between 50 kPa to 100 kPa, including (i) an inlet cell in fluid communication with said vessel having a hydrogen diffusion membrane between about 0.1 and 0.15 mm thick formed from an alloy containing palladium and silver and a membrane support means located within said cell formed from a stainless steel sponge having an average pore size of about 10 microns, (ii) a source of pressurized hydrogen fluidly connected to said cell through a first conduit for maintaining a supply of hydrogen within said cell pressurized to between about 50 kPa to 100 kPa, (iii) a vacuum regulator means fluidly connected across said first conduit, and (iv) a vacuum pump means fluidly connected to said first conduit at a point between said vacuum regulator means and said vessel for both evacuating hydrogen from the vessel during start-up of the apparatus, and for assisting the vacuum regulator in maintaining sub-atmospheric pressures of hydrogen within the vessel;

(c) means for monitoring the partial pressure of the hydrogen within the vessel, including (i) an outlet cell in fluid communication with said vessel having a hydrogen diffusion membrane between about 0.1 and 0.15 mm thick formed from an alloy containing palladium, and a membrane support means located within said cell formed from a stainless steel sponge having an average port size of about 10 microns, and (ii) means fluidly connected to said cell via a second conduit for sensing the pressure of the hydrogen within the vessel, whereby at least one of said cells includes a layer of palladium that covers all non-membrane parts of said cell, and wherein the palladium alloy in the membrane of said cell and said layer of palladium that covers all other parts of said cell may be used as an electrode.

6. The apparatus of claim 5, wherein said vacuum pump means is fluidly connected to said first conduit through a third conduit that includes a first valve means for controlling the amount of negative pressure said pump means exerts within said first conduit.

7. The apparatus of claim 6, further including a second valve means in said first conduit between said source of pressurized hydrogen and said vacuum regulator means for controlling the flow of hydrogen to said vacuum regulator means.

8. The apparatus of claim 7, further including a third valve connected to said first conduit between said vessel and the junction between said first and third conduits for fluidly connecting and disconnecting said inlet cell from the vacuum regulator means and the vacuum pump means.

* * * * *